US009775651B2

(12) United States Patent
Le Couedic et al.

(10) Patent No.: US 9,775,651 B2
(45) Date of Patent: Oct. 3, 2017

(54) VERTEBRAL FIXATION DEVICE AND SYSTEM FOR HOLDING A VERTEBRA ON A ROD, AND METHOD FOR IMMOBILIZING A LOOP USING SUCH A DEVICE

(71) Applicant: Implanet, Societe Anonyme, Martillac (FR)

(72) Inventors: Regis Le Couedic, Bordeaux (FR); Christian Baccelli, Saucats (FR)

(73) Assignee: Implanet, Societe Anonyme, Martillac (FR)

( * ) Notice: Subject to any disclaimer, the term of this patent is extended or adjusted under 35 U.S.C. 154(b) by 140 days.

(21) Appl. No.: 14/514,764

(22) Filed: Oct. 15, 2014

(65) Prior Publication Data

US 2015/0112389 A1    Apr. 23, 2015

(30) Foreign Application Priority Data

Oct. 18, 2013  (FR) ...................................... 13 60195

(51) Int. Cl.
*A61B 17/70*    (2006.01)
*A61L 31/02*    (2006.01)

(52) U.S. Cl.
CPC ...... *A61B 17/7053* (2013.01); *A61B 17/7001* (2013.01); *A61L 31/022* (2013.01)

(58) Field of Classification Search
CPC ...................................... A61B 17/70–17/7046
See application file for complete search history.

(56) References Cited

U.S. PATENT DOCUMENTS 4,887,596 A    12/1989  Sherman
4,950,269 A     8/1990  Gaines, Jr.
(Continued)

FOREIGN PATENT DOCUMENTS

EP    1138268 A1    10/2001
EP    2047813 A1     4/2009
(Continued)

OTHER PUBLICATIONS

International Search Report issued in corresponding International Application No. PCT/FR2011/000005 dated Mar. 3, 2011.
(Continued)

*Primary Examiner* — Jan Christopher Merene
*Assistant Examiner* — Steven Cotroneo
(74) *Attorney, Agent, or Firm* — Banner & Witcoff, Ltd.

(57) ABSTRACT

A vertebral fixation device and corresponding method of fixation hold a spinal vertebra on a rod. The device has a fixation element including a component of substantially U-shaped cross section with a first branch, a bottom and a second branch. A loop is formed by a flexible band for connecting the vertebra to the component, and which passes through recesses provided in the branches. Adjustable means for immobilizing the flexible band are provided. Those means include a connector screw having a head for longitudinal immobilization of the screw with respect to the first branch a thread for screwing in the second branch. A removable sleeve for passage of the screw, insertable in the first branch, in longitudinal abutment with the head of the screw is provided and presents a chamfered part designed to cooperate with the rod to compress the band between the rod and the bottom of the component.

22 Claims, 2 Drawing Sheets

(56) References Cited

U.S. PATENT DOCUMENTS

| | | | |
|---|---|---|---|
| 5,030,220 | A | 7/1991 | Howland |
| 5,129,388 | A | 7/1992 | Vignaud et al. |
| 5,176,680 | A | 1/1993 | Vignaud et al. |
| 5,335,400 | A | 8/1994 | Sales |
| 5,380,325 | A | 1/1995 | Lahille et al. |
| 5,383,905 | A | 1/1995 | Golds et al. |
| 5,498,264 | A * | 3/1996 | Schlapfer ............ A61B 17/7041 403/261 |
| 5,534,002 | A | 7/1996 | Brumfield et al. |
| 5,669,917 | A | 9/1997 | Sauer et al. |
| 5,676,665 | A | 10/1997 | Bryan |
| 5,782,831 | A | 7/1998 | Sherman et al. |
| 5,928,233 | A | 7/1999 | Apfelbaum et al. |
| 5,938,663 | A | 8/1999 | Petreto |
| 5,964,769 | A | 10/1999 | Wagner et al. |
| 5,976,133 | A * | 11/1999 | Kraus ................... A61B 17/171 606/54 |
| 6,086,590 | A | 7/2000 | Margulies et al. |
| 6,179,838 | B1 | 1/2001 | Fiz |
| 6,248,104 | B1 * | 6/2001 | Chopin ............... A61B 17/7041 606/267 |
| 6,248,106 | B1 | 6/2001 | Ferree |
| 6,290,700 | B1 | 9/2001 | Schmotzer |
| 6,296,643 | B1 | 10/2001 | Hopf et al. |
| 6,299,614 | B1 | 10/2001 | Kretschmer et al. |
| 6,309,390 | B1 | 10/2001 | Le Couedic et al. |
| 6,334,240 | B1 | 1/2002 | Li |
| 6,339,867 | B1 | 1/2002 | Azam |
| 6,402,751 | B1 | 6/2002 | Hoeck et al. |
| 6,514,255 | B1 | 2/2003 | Ferree |
| 6,554,831 | B1 | 4/2003 | Rivard et al. |
| 6,564,838 | B1 | 5/2003 | Cruickshank |
| 6,569,164 | B1 | 5/2003 | Assaker et al. |
| 6,656,185 | B2 | 12/2003 | Gleason et al. |
| 6,673,073 | B1 | 1/2004 | Schafer |
| 6,761,720 | B1 | 7/2004 | Senegas |
| 7,481,828 | B2 | 1/2009 | Mazda et al. |
| 8,128,635 | B2 | 3/2012 | Belliard et al. |
| 8,172,843 | B2 | 5/2012 | Baccelli et al. |
| 8,828,056 | B2 * | 9/2014 | Buss ................... A61B 17/7049 606/250 |
| 2002/0120272 | A1 | 8/2002 | Yuan et al. |
| 2003/0153915 | A1 | 8/2003 | Nekozuka et al. |
| 2004/0097942 | A1 | 5/2004 | Allen et al. |
| 2005/0131404 | A1 | 6/2005 | Mazda et al. |
| 2006/0206114 | A1 * | 9/2006 | Ensign ............... A61B 17/7034 606/278 |
| 2007/0123860 | A1 * | 5/2007 | Francis .............. A61B 17/7035 606/250 |
| 2009/0093843 | A1 | 4/2009 | Lemoine et al. |
| 2009/0182379 | A1 | 7/2009 | Baccelli et al. |
| 2009/0248077 | A1 | 10/2009 | Johns |
| 2010/0249845 | A1 | 9/2010 | Meunier et al. |
| 2012/0059377 | A1 | 3/2012 | Belliard |
| 2012/0271354 | A1 * | 10/2012 | Baccelli ............ A61B 17/7053 606/263 |

FOREIGN PATENT DOCUMENTS

| | | | |
|---|---|---|---|
| FR | 2694182 A1 | 2/1994 | |
| FR | 2842724 A1 | 1/2004 | |
| FR | 2890850 A1 | 3/2007 | |
| FR | 2954905 A1 | 1/2010 | |
| WO | 94/26192 A1 | 11/1994 | |
| WO | 02/09604 A1 | 2/2002 | |
| WO | 2006/034423 A2 | 3/2006 | |
| WO | 2009/013397 A1 | 1/2009 | |
| WO | 2009/130276 A1 | 10/2009 | |
| WO | 2009/141393 A1 | 11/2009 | |
| WO | WO2011/083261 | * 7/2011 | ............ A61B 17/70 |
| WO | 2013/001180 A1 | 1/2013 | |

OTHER PUBLICATIONS

International Search Report issued in corresponding International Application No. FR 1360195, dated Jul. 1, 2014.

\* cited by examiner

VERTEBRAL FIXATION DEVICE AND SYSTEM FOR HOLDING A VERTEBRA ON A ROD, AND METHOD FOR IMMOBILIZING A LOOP USING SUCH A DEVICE

The present invention relates to a vertebral fixation device for holding a spinal vertebra on a rod, of the type having an element for fixing on the rod, comprising a component of U-shaped or substantially U-shaped cross section with a first branch, a bottom and a second branch, comprising a loop which is formed by bringing together two end portions of a flexible hand for connecting the vertebra to the component, the component being provided on each of its branches with a recess for the end portions of the band to pass through, and having adjustable means for immobilizing the two end portions of the flexible band against the wall of the bottom of the U via the rod.

It also relates to a system comprising such a device and its associated rod.

It also concerns a method for immobilizing a closed loop with respect to a rod.

It has a particularly important but not exclusive application in the field of straightening the vertebral column of a patient having an abnormal curvature.

In order to straighten the arrangement, it is known to bring the lateral margins of the vertebrae on either side of the vertebral column together, by means of rods connecting them, either with screws, which are inserted into the vertebrae themselves, or hooks, which are introduced along the spinal canal.

However, these devices are not satisfactory.

The use of screws is possible only if the vertebrae are in good condition.

For its part, the use of hooks is problematic and poses a risk of important damage that could lead to paralysis of the patient.

To overcome these drawbacks, a system avoiding fixation screws or hooks has been proposed (FR 2 954 905).

The system comprises a flexible tie for fixing the vertebra on a linking piece, which is itself fixed to the rod.

Means are provided for immobilizing the ends or end portions of the loop passed round the vertebra by wedging a partially conical screw on the rod.

Although such a system makes it possible to obtain effective progressive clamping, there are some cases, especially when the rod is made of non-metallic material, where it may cause the flexible band to lose tension over the course of time.

The Present invention aims to overcome the disadvantages of the prior art.

To do so, it aims to make available a vertebral fixation device which, compared to the previously known devices, better meets the needs that arise in practice, especially in that it will permit better tensioning of the flexible band during the lifetime of the prosthesis and will thus keep the rod in position with respect to the vertebrae, in that it allows better flexibility and easier fitting of the end portions of the loop in the fixation component of the device on the rod, and in that it provides more varied possibilities of control on account of modular assembly, all this dependent on the material and thicknesses of the hand.

To this end, the invention basically proposes a vertebral fixation device for holding a spinal vertebra on a rod, having a fixation element comprising a component of U-shaped or substantially U-shaped cross section with a first branch, a bottom and a second branch, said branches having a distal portion, a loop formed by bringing together two end portions of a flexible hand for connecting the vertebra to the component, said component being provided on each of its branches with a recess for the end portions of the band to pass through, said recesses being situated opposite each other, and adjustable means for immobilizing the two end portions of the flexible band against, the wall of the bottom of the U via, the rod engaged on the component, comprising a connector screw with a body which connects the opposing distal portions of the two branches of the U, said body being provided, at one end, with a head for longitudinal screwing and immobilization of the screw with respect to a first branch of the U and, at the other end, with a screw thread for screwing in the second branch of the U, characterized in that the immobilizing means moreover have a removable sleeve for passage of the screw in the first branch of the U, in longitudinal abutment with the head of the screw, and having a chamfered part designed to cooperate with the rod along a generating line of the latter and to compress the end portions of the band between the rod and the bottom of the U when clamped.

Advantageously, the chamfered part is plane and forms a cant.

However, also advantageously, the chamfered part is curved (concave or convex), extending about an axis parallel (or substantially parallel) to that of the rod engaged on the component.

The fact that the part of the sleeve comprises a chamfered part, for example forming a cant acting on a generating line of the rod, will permit uniform clamping all along this generating line, which is thus in contact with the chamfer along a defined length and therefore not punctiform.

For this reason, the immobilization of the band has greater stability over the course of time, all the more so since a deformation of the rod will also be able to take place more widely, without a punch effect.

In advantageous embodiments, use is moreover and/or furthermore made of one or more of the following provisions:
  the component is formed as one piece;
  the cant forms an angle of between 30° and 80° with the plane perpendicular to the axis of the screw for example 60°;
  the inner wall of the bottom of the U is in the shape of a portion of a cylinder, terminated at one end by a rim in the direction parallel to the rod, permitting immobilization of the rod in the bottom of the U;
  the head of the clamping screw has a shoulder able to cooperate with the outer face of the upper part of the sleeve;
  the screw and the component being made of titanium, the sleeve and the rod are made of polymer material, and the flexible band is a polymer braid;
  the screw is made of titanium, the sleeve, the component and the rod being made of polymer material, and the flexible band is a polymer braid;
  the screw, the connecting component and the rod are made of titanium, the sleeve being made of polymer, and the flexible band is a polymer braid;
  the sleeve comprises a part in the shape of a cylinder at one end and terminates at the other end, situated towards the rod, in an elongate part narrower than the diameter of the cylinder portion having the chamfered part, the first branch of the U having an orifice for passage of the sleeve, at least partly having a shape complementing that of the upper part of said sleeve and extending toward the bottom of the U in order to form the recess for passage of the end portions of the band for the first branch of the U;

the narrower elongate part is beveled, symmetrical with respect to the transverse central plane of the sleeve, and has two opposite plane sides which between them form an angle α. The angle α is advantageously between 15° and 45°, for example 30°.

It has in fact been observed that the rod is rarely rectilinear in the plane orthogonal to the axis of the screw. The use of the punctiform contact is therefore more preferred by a person skilled in the art, since an implant having a wider contact zone can be difficult to assemble. A good compromise is obtained, by reducing the size of the contact generatrix by virtue of a beveled shape as per α;

the orifice for passage of the first branch of the U extends toward the bottom in order to form the recess for passage of the band by having two lateral sides symmetrical with respect to the axis of the component and forming between them an angle γ<α. The fact that this angle γ is less or slightly less (by a few degrees) than the angle α permits an adaptability of the system. The sleeve can thus position itself freely depending on the state of the zone it encounters when arriving in contact with the rod. This has the effect that, once the contact has been obtained between the rod and the cant, the bisector of the angle α is not necessarily contained by the transverse plane of the sleeve. Therefore, the recess is thus designed and dimensioned to permit a slight angular freedom of the sleeve on either side of the transverse plane;

the sleeve and the first branch of the U have means for indexing the position of the sleeve in said first branch.

The invention also relates to a system for straightening a vertebral column using a device as described, above.

It also relates to a system for straightening a spinal column comprising at least two devices as described above and at least one cylindrical rod on which the devices are fixed.

The invention also relates to a method by which a loop formed by the two ends of a flexible band is immobilized on a rod with the aid of a fixation component of U-shaped cross section, characterized in that the ends are immobilized between the bottom of the U and the rod by longitudinal screwing and immobilization of a screw through a removable sleeve for passage of the screw, said sleeve being in abutment, at one end, with the end of the branch of the U via the screw head and, at the other end, with the rod via a chamfered part.

Advantageously, since the sleeve is able to position itself freely in a through-recess iii a branch of the U, it is adjusted in position with the rod depending on the zone it encounters on arriving in contact with the rod.

Also advantageously, the screw and the sleeve are preassembled in such a way as to be rigidly connected, only retaining a freedom of rotation with respect to each other.

The invention will be better understood on reading the following description of an embodiment given below as a non-limiting example. The description makes reference to the accompanying drawings, in which.

Figure 1:
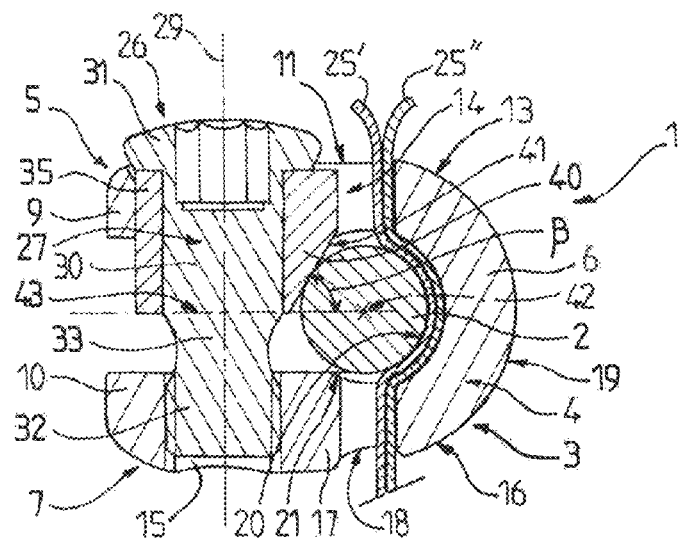
FIG. 1 is an axial and partial sectional view of the device with cylindrical rod, according to one embodiment of the invent ion.
Figure 2:
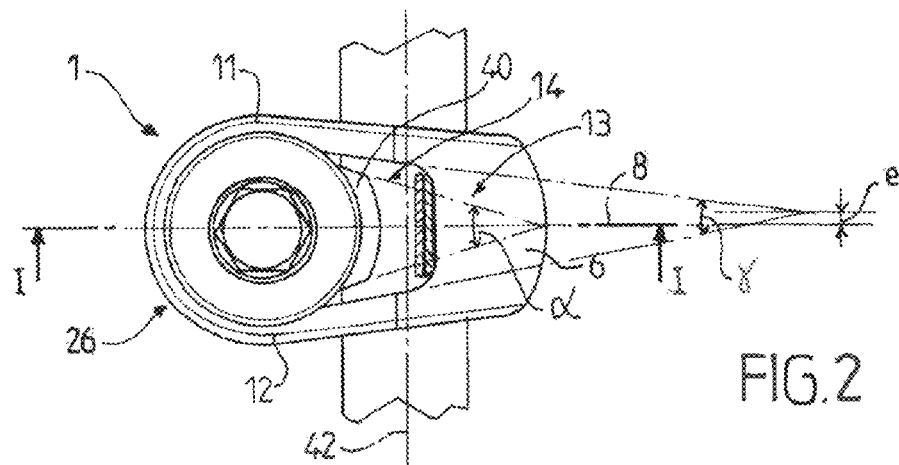
FIG. 2 is a plan view of the device from FIG. 1.

FIGS. 1 and 2 show a vertebral fixation device 1 for holding a spinal vertebra on a cylindrical rod 2.

It has a fixation element 3 comprising a component 4 made as one piece, with a substantially U-shaped cross section.

The component 4 has a first branch 5, a bottom 6 and a second branch 7.

The First and second branches 5, 7 of the U are composed of two openworked plates or tongues, for example of 5 mm thickness, each of them comprising two lateral parts which are symmetrical with respect to a transverse plane 3 (see FIG. 2).

Each plate has a semi-cylindrical distal portion 9, 10 at the end of each of said branches, connected to the bottom 6, for the first branch 5, by two arms 11 and 12 spaced apart from each other and delimiting, with the distal portion 9 at one end and the top 13 of the bottom 6, a recess 14 in the branch 5, of semi-cylindrical shape toward the distal portion and terminated toward the bottom by a substantially trapezoidal portion, of which the sides of the trapezoid form an angle γ, for example of 10°, and which will also be explained in detail below.

The second branch 7 for its part is formed by the distal portion 10, with a drilled bore 15, and is connected below 16 of the bottom by a rectangular portion 17 terminated by a recess 13 situated opposite the end of the recess 14 of the branch. 5, situated toward the bottom.

The bottom 6 for its part has, at one end, a rounded outer wall 19, of partially cylindrical (or partially tonic) surface, and, at the other end, an inner wall 20 homothetic or parallel to the outer wall 19, constituting the bottom of a cylindrical groove with a shape substantially complementing that of the rod 2.

In the embodiment more particularly described here, the wall 20 comprises, in the lower part, a longitudinal rim 21 in the direction parallel to the rod 2, formed by the upper edge of the rectangular portion 17, the rod being immobilized by the pressure of the wedge portion of the sleeve in a zone situated in the lower zone of the bottom of the U 6.

Figure 3:
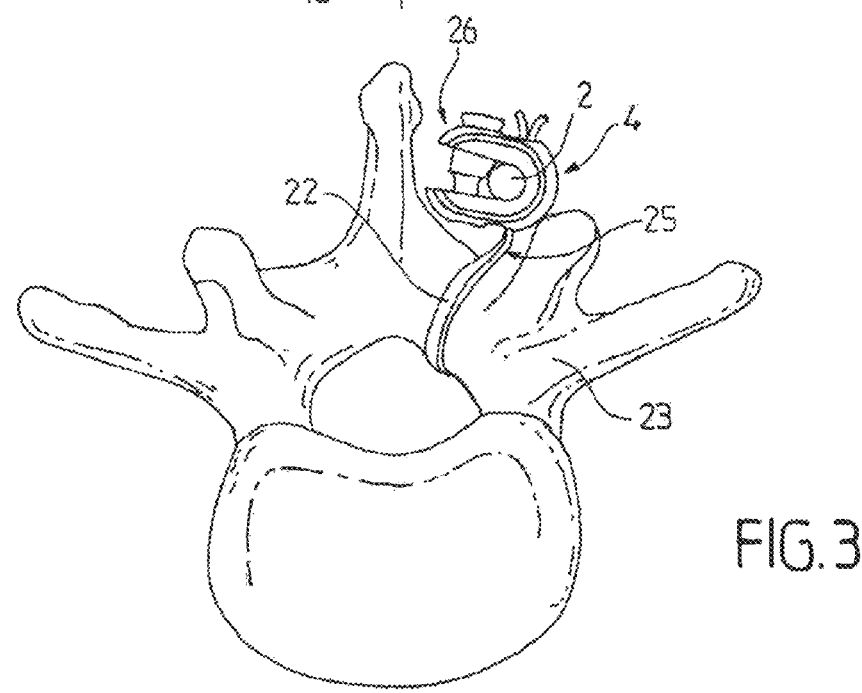
FIG. 3 shows, in a plan view, the device from FIG. 1 fixing a vertebra to a rod.
Figure 4:
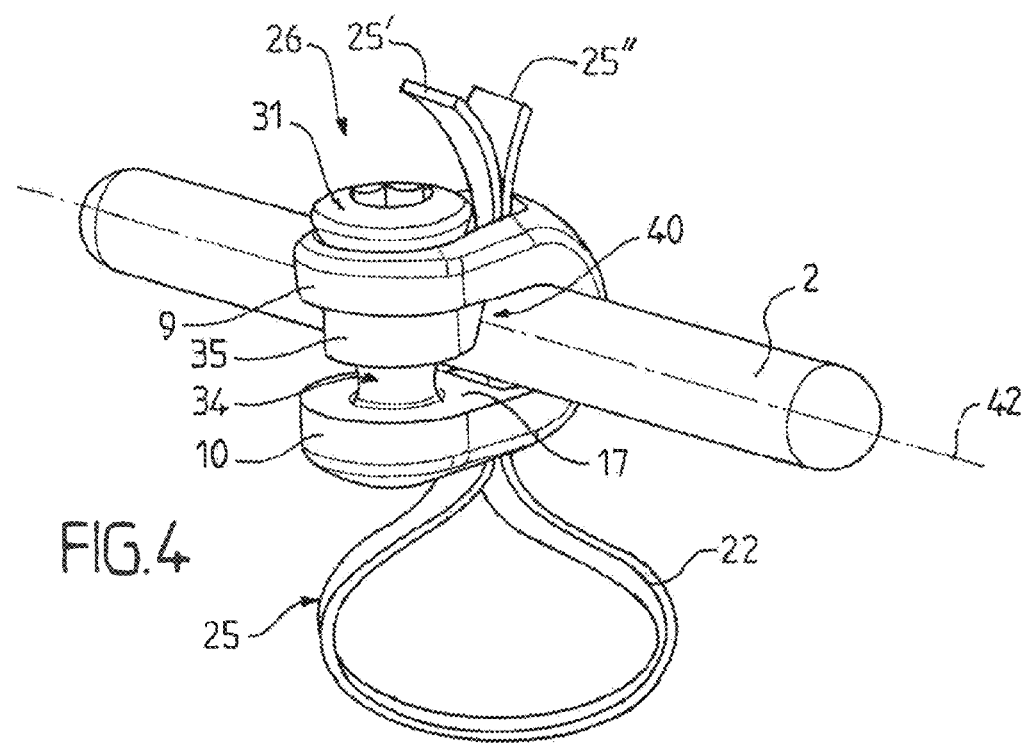
FIG. 4 is a perspective view of the system using the device from FIG. 1.

The fixation element 3 moreover comprises a loop 22 (see FIGS. 3 and 4) for fixing on a vertebra 23, and more particularly designed to be fixed on the lamina of the vertebra by passing through the spinal canal 24.

The loop is formed by a flexible band 25 of braided polymer, for example polyester with a thickness of 1 to 2 mm, a width of 6 mm, and a length of 30 cm.

More precisely, the loop 22 is formed by bringing together the two end portions 25', 25" of the flexible band 25 and thus ensures the connection of the vertebra. 23 to the fixation component 4.

It will be noted that the recesses 14 and 18 are situated (for their portions situated toward the bottom) opposite each other and each form a wide slit, for example 5 to 10 times wider than twice the thickness of band 25 for the recess 18; and even wider for the recess 14, in order to facilitate introduction of the band during the operation.

The device 1 also comprises means 26 for immobilizing the two end portions 25', 25" of the band 25 on the wall 20 of the bottom 6 of the U, via the rod 2.

Figure 5:
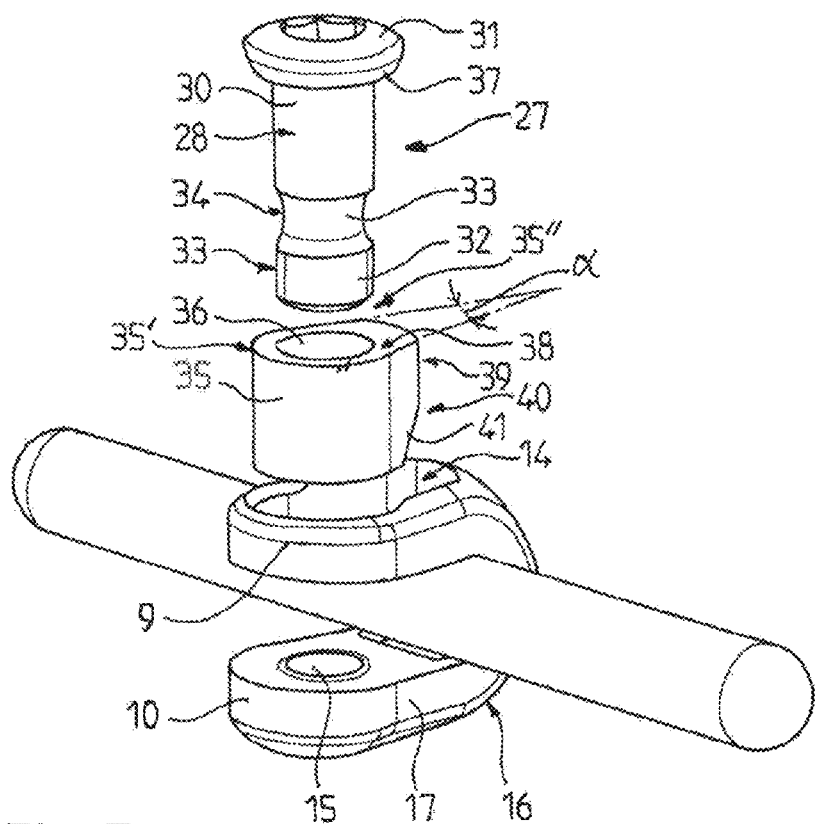
FIG. 5 is a perspective and exploded view of the system from FIG. 4.

More precisely, with reference to FIGS. 1 and 5, the immobilizing means 26 are adjustable and comprise a connector screw 27 with a body 28 designed to connect the opposite distal portions 9, 10 of the two branches 5 and 7 of the U.

The body 28 extends about a longitudinal axis 29 and comprises a cylindrical upper part 30 terminated by a head 31 for the longitudinal screwing and immobilization of the screw with respect to the first branch 5.

The body 26 also has a cylindrical lower part 32, provided with a thread for screwing in the threaded bore 15 of the second branch 7 of the U.

In the embodiment described here, the upper part 30 and the lower part 36 are connected to each other by an intermediate part 33 forming an annular groove 34.

The groove 34 extends, for example, along a height of the screw 27 of between ⅙th and ⅓ thereof, and it has a shallow depth, for example of 0.5 mm.

According to the embodiment more particularly described here, the immobilizing means 26 moreover have a removable sleeve 35 for passage of the screw 27.

The sleeve has an outer shape complementing the recess 14 toward the distal portion 9 and is designed to be inserted with slight friction into said recess 14.

It has a bore 36 (cf. FIG. 5) for passage of the screw 27.

For its part, the head 31 of the clamping screw 27 has a shoulder 37 able to cooperate with the upper outer face 38 of the sleeve.

More precisely, the sleeve 35 comprises an upper part 39 and a lower part 40, both on one side as a cylinder portion 35' and on the other side as a more elongate beveled portion 35", and in the shape of a toric sector in an angle range α of between 20° and 90°, for example 30° (cf. FIG. 2).

The lower part 40 of the beveled portion 35" of the sleeve 35 is chamfered, parallel to the axis 29 of the screw and of the bore, in order to form a cant 41 toward the bottom of the U. The cant 41 is included in a plane parallel to the axis 42 of the rod 2 and is designed to cooperate with the rod 2 and to compress the end portions 25', 25" of the band 25 between the rod 2 and the bottom 20 of the U during clamping.

It forms an angle β of between 30° and 80° with the plane 43 perpendicular to the axis 29 of the screw, here 60°.

The more elongate beveled portion of the sleeve 35 cooperates symmetrically by friction with the opposing walls of the recess 14 of the first branch 5 of the U and can either form means for indexing the position of the sleeve 35 in the first branch, or, by contrast, as in the case described here, can have a clearance, on account of the difference between the angles α and γ (with γ<α), which can lead (cf. FIG. 2) to an offset e between the plane 8 and the vertex of the angle γ.

A difference of this kind permits an adjustment that makes the device easier to fit in place.

The way in which the device 1 functions will now be described, again with reference more particularly to FIGS. 1 and 5.

It will allow the loop 22 formed by the two ends 25', 25" of the flexible band 25 to be immobilized tightly in position on the rod 2 with the add of the fixation component 4 in order to allow said loop 22 to be fixed mechanically around the vertebra 23.

The use of such a device is indicated particularly in the context of surgical treatment of scoliosis of the spine, using two parallel rods, for example, which, are placed on either side of the spinal column of the patient.

However, such a device may also prove very useful in degenerative conditions, as reinforcement for pedicle screws implanted in a bone of poor quality. In other cases of primary degenerative pathologies, it may be conceivable for such a device to be used on its own as a replacement for the pedicle screws. From this perspective, and in order to maintain a certain degree of flexibility of the portion of the vertebral column on which surgery is performed, it may be desirable to use rods made of polymer with a modulus of elasticity close to that of bone. In this case, it is necessary to optimize the contact with the rod in order to avoid creep, which may be prejudicial to the long-term survival of the system.

After the dorsal region of the patient (not shown) has been opened up in order to access the vertebrae 23 that are to be straightened, the surgeon fits the two rode 2 in place.

He then fits in place the devices 1 made of biocompatible material.

The description given below here concerns the placement of a single device. It goes without saying that the other devices will be fitted in place similarly and with progressive balancing.

In the example described, the fixing screw 27 and the sleeve 35 are made of titanium, the rod 2 and the connecting component 4 being made of titanium.

The surgeon first of all forms the loop 22 loosely around the vertebra 23, then passes the end portions 25', 25" of the band 25 through the recesses 14 and 18 of the component 4 and allows them to emerge at the other side in relation to the loop.

He then engages the device onto the rod 2, which will slightly compress the two end portions 25' 25" of the band against the bottom of the U, which allows an initial adjustment of the width of the loop.

He then inserts the removable sleeve 35 with slight friction into the orifice 14 of the first branch, positioning the elongate part 40 of the sleeve 35 in alignment with the corresponding opposite narrowing of said orifice of the first branch, the difference in angle value between α and γ permitting an adjustment with the rod.

He then introduces the screw 27 into the bore of the sleeve until it cooperates with the bore 15 of the second branch 7.

In another embodiment, the screw 27 and the sleeve 35 are pre-assembled and introduced simultaneously.

The screw is screwed in progressively, which will push the chamfer 41 against the rod along a straight generating line of said rod.

The loop 22 is then brought closer to the rod. 2, which has the result of bringing the vertebra 23 gradually closer to the rod 2 and of straightening the spinal column, the friction of the end portions against the bottom of the U being dosed.

In another embodiment corresponding to the case of a use in degenerative conditions, there is no actual reduction phase. It is simply a matter of tensioning the braid while the rod is already correctly positioned. There is therefore only minimum coming together between the vertebra 23 and the rod 2.

When the desired position is obtained, final screwing takes place until longitudinal abutment of the shoulder 37 of the head 31 of the screw against the upper edge of the sleeve 38.

As is evident, and as also results from the foregoing, the present invention is not limited to the embodiments that are more particularly described. On the contrary, it encompasses all the variants thereof and especially those where two or more rods are fixed in succession or on either side of the vertebral column, and one where the screw is of a different shape and/or the cant is not plane but ensures a linear contact with the rod, that is to say the cant is formed by a curved section around an axis parallel to the axis of the rod 2.

Such an arrangement will permit contact on a longitudinal surface possibly greater than a simple line and in this way will further improve the stability of the link.

The invention claimed is:

1. A vertebral fixation device for holding a spinal vertebra on a rod having:
    a fixation element comprising a U component of a U-shaped cross section, said U component comprising a first branch, a bottom having an inner wall and a second branch, said first and second branches each having a distal portion,
    a flexible band having two opposite end portions arranged to form a loop by bringing together said opposite end portions of said flexible band, the flexible band for connecting the vertebra to the U component,
    the first branch has a first recess, the second branch has a second recess, said recesses being situated opposite each other and allowing passage of said two opposite end portions of the flexible band, and
    adjustable means for immobilizing the two end portions of the flexible band against the inner wall of the bottom of the U component via the rod engaged on the U component,
    wherein said first recess is of semi-cylindrical shape on a side of the corresponding distal portion of the first branch,
    said adjustable means comprising a connector screw having a body with an axis, said connector screw connecting the distal portions of said first and second branches of the U component, said body being provided integrally, at one end, with a head for longitudinal screwing and immobilization of said connector screw with respect to said first branch of the U component and, at the other end, with a screw thread for screwing in a corresponding bore of said second branch of the U component,
    wherein said adjustable means further comprises a removable sleeve for passage of said connector screw, the removable sleeve being slidably mounted in said first recess, in longitudinal abutment with the head of the screw, and having a chamfered part that cooperates with the rod to compress said end portions of the flexible band between the rod and the inner wall of the bottom of the U component upon screwing the connector screw into the bore of the second branch of the U component.

2. The device according to claim 1, wherein the chamfered part is planar and forms a cant.

3. The device according to claim 2, wherein the cant forms an angle ($\beta$) of between 30° and 80° with a plane perpendicular to the axis of the screw.

4. The device according to claim 3, wherein the cant forms the angle ($\beta$) of 60°.

5. The device according to claim 1, wherein the chamfered part is concave or convex extending about an axis parallel or substantially parallel to the rod engaged on the U component.

6. The device according to claim 1, wherein the U component is formed as one piece.

7. The device according to claim 1, wherein the inner wall of the bottom of the U component is in the shape of a portion of a cylinder, terminated at one end by a rim in the direction parallel to the rod, permitting immobilization of said rod in the bottom of the U component.

8. The device according to claim 1, wherein the head of the connector screw has a shoulder able to cooperate with an outer face of an upper part of the removable sleeve.

9. The device according to claim 1, wherein the screw, the sleeve and the U component are made of titanium, and the flexible band is a polymer braid.

10. The device according to claim 1, further comprising a said rod, wherein the screw and the U component are made of titanium, the sleeve and the rod are made of polymer, and the flexible band is a polymer braid.

11. The device according to claim 1, further comprising a said rod, wherein the screw is made of titanium, the sleeve and the rod and the U component are made of polymer, and the flexible band is a polymer braid.

12. The device according to claim 1, further comprising a said rod, wherein the screw, the U component and the rod are made of titanium, the sleeve is made of polymer, and the flexible band is a polymer braid.

13. The device according to claim 1, wherein the sleeve comprises an upper part in the shape of a cylinder portion at one end and terminates at the other end in a narrower elongate part having the chamfered part, the first branch of the U component having an orifice for passage of the sleeve, at least partly having a shape complementing that of the upper part of said sleeve and extending toward the bottom of the U component in order to form the recess for passage of the end portions of the band for the first branch of the U component.

14. The device according to claim 13, wherein the narrower elongate part is beveled, symmetrical with respect to the transverse central plane of the sleeve, and has two opposite plane sides which between them form an angle $\alpha$ of between 15° and 45°.

15. The device according to claim 14, wherein the through-orifice of the first branch of the U component extends toward the bottom in order to form the recess for passage of the band by having two lateral sides symmetrical with respect to the axis of the U component and forming between them an angle $\gamma < \alpha$.

16. The device according to claim 1, wherein the sleeve and the first branch of the U component have means for indexing the position of the sleeve in said first branch.

17. The device according to claim 1, wherein the sleeve comprises an upper part and a lower part, said upper part and lower part having on one side a cylinder portion, arranged to slidably cooperate with the first recess on the side of the distal end of said first branch, and on the other side an elongated bevelled portion forming at least partially the chamfered part.

18. The device according to claim 1, further comprising a said rod, wherein the rod has an axis, and the chamfered part is chamfered in a direction parallel to the axis of the connector screw, and forms a cant included in a plane parallel to the axis of the rod.

19. A system for straightening a vertebral column, comprising at least two devices according to claim 2, wherein the system has at least one cylindrical rod on which the devices are fixed.

20. A method by which a loop formed by the ends of a flexible band is immobilized on a rod with the aid of a fixation component having a U-shaped cross-section, the method comprising;
    providing a U component comprising a first branch, a bottom and a second branch, said first and second branch each having a distal portion, said first branch having a first recess of semi cylindrical shape on a side of the corresponding distal portion of the first branch, said second branch having a bore;
    passing the ends through the first recess in the first branch;
    inserting the rod between the first and second branches;

slidably mounting a removable sleeve having a chamfered part to the first recess, the sleeve being in contact with said first recess on the side of the distal end of said first branch and the chamfered part being in contact with the rod; and immobilizing the ends between the bottom of the U-component and the rod by screwing and immobilizing a screw through the removable sleeve, said screw having a screw thread which is screwed into the bore of said second branch.

21. The method according to claim 20, wherein the removable sleeve is freely positioned in said first recess and is adjustable relative to the rod.

22. The method according to claim 20, wherein the screw and the sleeve are pre-assembled in such a way as to be rigidly connected, only retaining a freedom of rotation with respect to each other.

* * * * *